(12) United States Patent
Takayanagi et al.

(10) Patent No.: US 6,340,656 B1
(45) Date of Patent: Jan. 22, 2002

(54) LIGHT, EXTRUDED COMPOSITIONS CONTAINING A LIGHT, EXTRUDABLE, CERAMIC CARRIER, METHODS FOR THEIR USE, AND PROCESSES FOR THEIR PREPARATION

(75) Inventors: Norikazu Takayanagi, Aichi; Masaomi Kimpara, Shizuoka; Munehiro Suzuki, Aichi, all of (JP)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/501,554

(22) Filed: Feb. 9, 2000

Related U.S. Application Data

(60) Provisional application No. 60/119,650, filed on Feb. 11, 1999.

(51) Int. Cl.$^7$ ................................................ A01N 25/08
(52) U.S. Cl. ........................ 504/367; 514/770; 514/949
(58) Field of Search ........................ 504/367; 514/770, 514/949

(56) References Cited

U.S. PATENT DOCUMENTS

| | | | | |
|---|---|---|---|---|
| 3,719,467 A | * | 3/1973 | Loux | 71/120 |
| 4,714,712 A | * | 12/1987 | Matsuo et al. | 514/531 |
| 5,563,159 A | * | 10/1996 | Kusaba et al. | 514/346 |
| 5,830,827 A | * | 11/1998 | Maeda | 504/215 |
| 5,833,733 A | | 11/1998 | Wada et al. | 71/27 |
| 5,977,023 A | * | 11/1999 | Inoue et al. | 504/116 |
| 6,071,858 A | * | 6/2000 | Modrcin et al. | 504/134 |
| 6,083,873 A | * | 7/2000 | Fukuda et al. | 504/105 |

FOREIGN PATENT DOCUMENTS

| | | |
|---|---|---|
| EP | 0 280289 A | 8/1988 |
| JP | 6-321704 | 11/1994 |
| WO | 93 25074 A | 12/1993 |
| WO | 95 08265 | 3/1995 |

* cited by examiner

Primary Examiner—S. Mark Clardy
(74) Attorney, Agent, or Firm—Barbara V. Maurer

(57) ABSTRACT

The present invention provides light, extruded compositions and methods for their preparation. The light, extruded compositions comprise at least one agricultural compound; a light, extrudable, ceramic carrier; and at least one surface active agent. The present invention also provides a method for applying agricultural compounds to the water of paddy fields by localized application(s) of the light, extruded compositions to the water surface of the paddy fields.

33 Claims, No Drawings

LIGHT, EXTRUDED COMPOSITIONS CONTAINING A LIGHT, EXTRUDABLE, CERAMIC CARRIER, METHODS FOR THEIR USE, AND PROCESSES FOR THEIR PREPARATION

This application claims priority from copending provisional application(s) serial No. 60/119650 filed on Feb. 11, 1999.

BACKGROUND OF THE INVENTION

Solid agricultural compositions which may be applied to the surface water of paddy fields are known in the art (see, for example, U.S. Pat. No. 5,833,733 and JP 6-321704).

U.S. Pat. No. 5,833,733 describes agrochemical formulations for water surface application. These formulations require: (1) a solid core material having an apparent specific density of less than 1 and a particle diameter within the range from about 300 μm to about 1,400 μm; and (2) at least one oily substance. However, this patent does not disclose any extruded formulations. It is difficult to prepare extruded formulations containing large particle sizes of low-density carriers because large, low-density particles are not entirely stable to the conditions encountered during extrusion processes. In addition, the use of oily substances is not entirely satisfactory because oily substances may reduce the uniformity of the extruded composition and/or may decrease the flash point of the finished product.

JP 6-321704 describes pesticidal formulations for water surface application. The formulations described in JP 6-321704 require hollow, glass bodies having an average particle diameter of 100 μm or less. However, that application does not disclose any extruded formulations. It is difficult to prepare extruded formulations containing hollow, glass bodies because hollow, glass bodies are not entirely stable to the conditions encountered during extrusion processes.

It is, therefore, an object of the present invention to provide a light, extruded composition which avoids the use of low-density carriers having a particle range of about 300 μm to 1,400 μm; oily substances; and/or hollow, glass bodies.

It is also an object of the present invention to provide a method for applying at least one agricultural compound to the water of paddy fields by applying to the water surface of the paddy fields a light, extruded composition.

It is a further object of this invention to provide a process for the preparation of a light, extruded composition.

Other objects and advantages of the present invention will be apparent to those skilled in the art from the description below and the appended claims.

SUMMARY OF THE INVENTION

The present invention relates to a light, extruded composition which comprises at least one agricultural compound; a light, extrudable, ceramic carrier; and at least one surface active agent.

The present invention also relates to a method for applying at least one agricultural compound to the water of paddy fields which method comprises applying to the water surface of the paddy fields a light, extruded composition comprising at least one agricultural compound; a light, extrudable, ceramic carrier; and at least one surface active agent.

The present invention further provides a process for the preparation of the light, extruded compositions of this invention.

DETAILED DESCRIPTION OF THE INVENTION

The light, extruded compositions of this invention comprise at least one agricultural compound; a light, extrudable, ceramic carrier; and at least one surface active agent.

Preferred light, extruded compositions of the present invention are those comprising at least one agricultural compound; a light, extrudable, ceramic carrier; at least one surface active agent; a mineral carrier; and a binder.

More preferred light, extruded compositions of the present invention are those comprising, on a weight to weight basis, about 0.5% to 75% of one or more agricultural compound(s); about 15% to 90% of a light, extrudable, ceramic carrier; about 2% to 20% of one or more surface active agent(s); about 1% to 30% of a mineral carrier; and about 0.1% to 10% of a binder.

Most preferred light, extruded compositions of this invention are those comprising, on a weight to weight basis, about 1% to 60% of one or more agricultural compound(s); about 20% to 60% of a light, extrudable, ceramic carrier; about 2% to 15% of one or more surface active agent(s); about 1% to 15% of a mineral carrier; and about 0.5% to 5% of a binder.

The light, extrudable, ceramic carrier is an especially important element of the present compositions because: (1) the light, extrudable, ceramic carrier lowers the density of the compositions, and (2) the light, extrudable, ceramic carrier does not lose its desirable low density property when subjected to the process steps used to prepare the compositions of this invention. In contrast, hollow, glass bodies, which are used in conventional light, solid compositions, are not entirely stable to conditions encountered during the preparation of light, extruded compositions. In particular, hollow, glass bodies are not entirely stable to the pressure and shearing forces encountered in processes which include an extrusion step.

Light, extrudable, ceramic carriers suitable for use in this invention include ceramic carriers having a density less than the medium to which the light, extruded compositions are to be applied. The light, extrudable, ceramic carrier typically has a density of less than 1 $g/cm^3$, and preferably has a density of from about 0.5 $g/cm^3$ to 0.8 $g/cm^3$. In a preferred embodiment of the present invention, the light, extrudable, ceramic carrier is prepared by: (1) heating a naturally occuring mineral composition which comprises silicon(IV) oxide, aluminum oxide, calcium oxide, iron(III) oxide and titanium(IV) oxide; (2) selecting particles having a density of from about 0.5 $g/cm^3$ to 0.8 $g/cm^3$; and (3) sieving the particles to obtain a light, extrudable, ceramic carrier having the desired particle size range. In another preferred embodiment of this invention, the light, extrudable, ceramic carrier is prepared from a composition which comprises, on a weight to weight basis, about 50% to 60% silicon(IV) oxide, about 25% to 45% aluminum oxide, about 0.1% to 6% calcium oxide, about 0.1% to 3% iron(III) oxide and about 0.1% to 2% titanium(IV) oxide. To ensure that the light, extrudable, ceramic carrier retains its desirable low density property, the light, extrudable, ceramic carrier preferably has a pressure strength (>40% survival) greater than about 150 kg/cm$^2$, and more preferably greater than about 500 kg/cm$^2$. The light, extrudable, ceramic carrier of the present invention preferably has an average particle size of about 20 $\mu$m to 300 $\mu$m, and more preferably, about 100 $\mu$m to 250 $\mu$m. Examples of light, extrudable, ceramic carriers suitable for use in the compositions of this invention include the E-SPHERES line of hollow, ceramic spheres commercially available from Taiheiyo Cement, Tokyo, Japan.

Agricultural compounds suitable for use in the light, extruded compositions of this invention include, but are not limited to, herbicides, insecticides, acaricides, nematicides, fungicides, molluscicides, plant growth regulators, safeners, algicides, and mildewicides, and mixtures thereof.

Herbicides suitable for use in the compositions of this invention include, but are not limited to, 2,4-D, 2,4-D-2-ethylhexyl, 2,4-D-isobutyl, 2,4-D-butyl, 2,4-D-calcium, 2,4-D-dimethylammonium, 2,4-D-diolamine, 2,4-D-isooctyl, 2,4-D-isopropyl, 2,4-D-potassium, 2,4-D-sodium, 2,4-D-trolamine, azimsulfuron, bensulfuron-methyl, bentazone, benzofenap, bifenox, bromobutide, butachlor, cafenstrole, chlormethoxynil, chlornitrofen, chlorthiamid, cinmethylin, cinosulfuron, clomeprop, cyclosulfamuron, cyclosulfamuron sodium salt, cyhalofop-butyl, dimepiperate, dimethametryn, dithiopyr, dymron, esprocarb, ethoxysulfuron, etobenzanid, fentrazamid, imazosulfuron, MCPA, MCPA-butyl, MCPA-calcium, MCPA-dimethylammonium, MCPA-isooctyl, MCPA-potassium, MCPA-sodium, MCPB, MCPB-ethyl, MCPB-sodium, MCPCA, mefenacet, molinate, napro-anilide, oxadiazon, oxaziclomefone, pendimethalin, pentoxazone, piperophos, pretilachlor, prometryn, propanil, pyrazolate, pyrazosulfuron-ethyl, pyrazoxyfen, pyributicarb, simetryn, swep, thenylchlor, and thiobencarb, and mixtures thereof. Cyclosulfamuron, cafenstrole, and dymron, and mixtures thereof are preferred herbicides for use in the compositions of this invention.

Insecticides suitable for use in the compositions of this invention include, but are not limited to, acephate, alpha-cypermethrin, benfuracarb, bensultap, BPMC, buprofezin, carbaryl, carbofuran, carbosulfan, cartap, chlorfenapyr, chlorfenvinphos, chlorpyrifos-methyl, chlorpyrifos, cyanofenphos, cycloprothrin, diazinon, dimethoate, dioxabenzofos, disulfoton, EPN, ethofenprox, fenitrothion, fenthion, furathiocarb, isoprocarb, methyl isothiocyanate, isoxathion, malathion, methomyl, metolcarb, monocrotophos, nitenpyram, phenthoate, pirimiphos-ethyl, pirimiphos-methyl, propaphos, propoxur, pyraclofos, pyridaphenthion, quinalphos, tetrachlorvinphos, thiocyclam, thiodicarb, trichlorphon, vamidothion, XMC, xylylcarb, and 1-[1-(p-chlorophenyl)-2-fluoro-4-(4-fluoro-3-phenoxyphenyl)-2-butenyl]cyclopropane (R,S)-(Z), and mixtures thereof.

Fungicides suitable for use in the compositions of this invention include, but are not limited to, benomyl, captan, diclomezine, edifenphos, fenoxanil, ferimzone, flutolanil, fthalide, iprobenfos, iprodione, isoprothiolane, kasugamycin, kasugamycin hydrochloride hydrate, mepronil, metalaxyl, methominostrobin, oxolinic acid, pencycuron, probenazole, pyroquilon, tecloftalam, thiophanate-methyl, TPN, tricyclazole, triflumizole, and validamycin, and mixtures thereof.

Surface active agents suitable for use in the compositions of the present invention include, but are not limited to, alkyl benzene sulfonates, alkyl naphthalene sulfonates, lignosulfonates, naphthalene sulfonate-formaldehyde condensates, alkyl naphthalene sulfonate-formaldehyde condensates, polyoxyethylene alkyl ethers, polyoxyethylene alkyl ether sulfates, polyoxyethylene alkyl ether phosphates, polyoxyethylene alkyl aryl ethers, polyoxyethylene alkyl aryl ether sulfates, polyoxyethylene alkyl aryl ether phosphates, polycarboxylates, sodium tripolyphosphates, hexameta phosphates, phenol sulfonates, alkyl sulfates, dialkyl sulfosuccinates, alkyl ether sulfates and acetylene glycols and mixtures thereof. Preferred surface active agents include alkyl naphthalene sulfonates such as a sodium alkyl naphthalene sulfonate and the like; polycarboxylates; naphthalene sulfonate-formaldehyde condensates such as a sodium naphthalene sulfonate-formaldehyde condensate and the like; and dialkyl sulfosuccinates such as a sodium alkyl sulfonated alkylate and the like; and mixtures thereof.

Mineral carriers suitable for use in the compositions of this invention include, but are not limited to, bentonites such as calcium bentonite and sodium bentonite; montmorillonite clays; kaolin clays; diatomaceous earth; and talc; and mixtures thereof. Sodium bentonite is a preferred mineral carrier.

Binders suitable for use in the compositions of the present invention include, but are not limited to, cellulose based binders such as sodium carboyxmethyl cellulose, hydroxy methyl cellulose, methyl cellulose, ethyl cellulose, and the like; dextrin; starch; poly(vinyl alcohol); sodium alginate; sodium polyacrylate; and gums such as xanthan gum, welan gum, gum arabic and the like; and mixtures thereof. Sodium carboxymethyl cellulose is a preferred binder.

The present invention further provides herbicidal compositions for the control of undesirable plant species in the presence of rice plants. Preferred herbicides for the control of undesirable plant species in the presence of rice plants include cyclosulfamuron, cafenstrole, dymron, pentoxazone, fentrazamid, dithiopyr, oxaziclomefone, clomeprop, and cinmethylin, and mixtures thereof. Preferred rice herbicide mixtures for use in the compositions of this invention include: cyclosulfamuron/cafenstrole/dymron mixtures; cyclosulfamuron/pentoxazone mixtures; cyclosulfamuron/fentrazamid/dymron mixtures; cyclosulfamuron/dithiopyr mixtures; cyclosulfamuron/oxaziclomefone mixtures; cyclosulfamuron/oxaziclomefone/clomeprop mixtures; and cyclosulfamuron/cinmethylin mixtures.

A preferred herbicidal composition of this invention comprises, on a weight to weight basis, about 0.2% to 7% cyclosulfamuron; about 10% to 20% cafenstrole; about 25% to 35% dymron; about 25% to 45% of a light, extrudable, ceramic carrier which: (1) is prepared from a composition which comprises silicon(IV) oxide, aluminum oxide, calcium oxide, iron(III) oxide and titanium(IV) oxide, (2) has an average particle size of about 100 $\mu$m to 250 $\mu$m, and (3)

has a pressure strength greater than about 150 kg/cm$^2$; about 4% to 8% of a sodium alkyl naphthalene sulfonate; about 0.5% to 2% of a mixture of a polycarboxylate and a sodium naphthalene sulfonate-formaldehyde condensate; about 1% to 3% of a sodium alkyl sulfonated alkylate; about 3% to 8% sodium bentonite; and about 1% to 3% sodium carboxymethyl cellulose.

The light, extruded compositions of this invention may be prepared by:

(a) mixing at least one agricultural compound; a light, extrudable, ceramic carrier; at least one surface active agent; optionally a mineral carrier; and optionally a binder with water to obtain an extrudable mixture;

(b) extruding the extrudable mixture from step (a) to obtain an extrudate; and (c) drying the extrudate to obtain the light, extruded compositions of this invention.

Advantageously, the light, extrudable, ceramic carrier of the present invention is stable during the extrusion process and retains its desirable low-density property. In contrast, light, carriers made from materials such as glass and/or having a large average particle size are not entirely stable during the extrusion process and lose a significant amount of their desirable low density properties.

The light, extruded compositions of this invention may be applied directly to water, soil or other media for application of the agricultural compound(s). In particular, the light, extruded compositions of the present invention are useful for applying agricultural compounds to the water of paddy fields. Paddy-wide application of one or more agricultural compounds may be achieved by localized application(s) of the light, extruded compositions of this invention to the water surface of paddy fields. Accordingly, the present invention provides a method for applying at least one agricultural compound to the water of paddy fields by applying to the water surface of the paddy fields a light, extruded composition comprising at least one agricultural compound; a light, extrudable, ceramic carrier; and at least one surface active agent.

The light, extruded compositions of this invention may be packaged in a contained, water-soluble delivery system and applied to the water surface of paddy fields in water-soluble, packaged form. Water-soluble delivery systems include, but are not limited to, water-soluble poly(vinyl alcohol) bags (PVA bags), water-soluble paper bags, and water-soluble bottles, and the like.

Alternatively, the light, extruded compositions of this invention may be packaged in uncontained systems and applied by hand, spoon, aerial or mechanical application from the uncontained system. Uncontained systems include, but are not limited to, bags, including foil lined bags, tubes including paper tubes, and hoppers, either hand held or attached to a mechanical applicator, such as a cultivator.

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1

Preparation of Light, Extruded Compositions

A mixture of cyclosulfamuron (3.3 g, average particle size less than 20 μm); cafenstrole (15.75 g, average particle size less than 5 μm); dymron (31.50 g); sodium bentonite (4.8 g, particle size range 5–10 μm, commercially available as bentonite-Na type from Kunimine Co., Tokyo, Japan); NEWKALGEN WG-1 a sodium alkyl naphthalene sulfonate (6.0 g, commercially available from Takemoto Oil and Fat Co., Aichi, Japan); and CELLOGEN WS-C a sodium carboxymethyl cellulose (1.5 g, commercially available from Dai-Ichi Kogyo Seiyaku Co., Kyoto, Japan) is blended to obtain a first mixture. E-SPHERES SL-180 hollow ceramic spheres (34.15 g, average particle size 115 μm, commercially available from Taiheiyo Cement, Tokyo, Japan) are added to the first mixture and blended to obtain a second mixture. NEWKALGEN TG-285 a mixture of a polycarboxylate and a sodium naphthalene sulfonate-formaldehyde condensate (1.0 g, commercially available from Takemoto Oil and Fat Co.); NEWKALGEN EP-70G a sodium alkyl sulfonated alkylate (2.0 g, commercially available from Takemoto Oil and Fat Co.); and water are added to the second mixture and blended to obtain an extrudable mixture. The extrudable mixture is passed through a basket extruder to obtain extruded material. The extruded material is dried and sieved to give the light, extruded composition identified as composition 1 in Table I.

Using essentially the same process, the light, extruded compositions identified as compositions 2–16 in Tables I–V are obtained.

TABLE I

Light, Extruded Compositions
Ingredient/%wt/wt

| Comp. | Cyclo-sulfamuron | Cafen-strole | Dymron | Sodium Bentonite | NEWKALGEN WG-1 | CELLOGEN WS-C | E-SPHERES/ (Avg. particle size μm) | NEWKALGEN TG-285 | NEWKALGEN EP-70G |
|---|---|---|---|---|---|---|---|---|---|
| 1 | 3.30 | 15.75 | 31.50 | 4.80 | 6.00 | 1.50 | 34.15/ (115)[1] | 1.00 | 2.00 |
| 2 | 3.30 | 15.75 | 31.50 | 4.80 | 6.00 | 1.50 | 34.15/ (103)[2] | 1.00 | 2.00 |
| 3 | 3.30 | 13.13 | 26.25 | 5.00 | 6.00 | 1.50 | 41.82/ (115)[1] | 1.00 | 2.00 |
| 4 | 2.64 | 12.60 | 25.20 | 6.06 | 6.00 | 1.50 | 43.00/ (103)[2] | 1.00 | 2.00 |

TABLE I-continued

Light, Extruded Compositions
Ingredient/%wt/wt

| Comp. | Cyclo-sulfamuron | Cafen-strole | Dymron | Sodium Bentonite | NEWKALGEN WG-1 | CELLOGEN WS-C | E-SPHERES/ (Avg. particle size μm) | NEWKALGEN TG-285 | NEWKALGEN EP-70G |
|---|---|---|---|---|---|---|---|---|---|
| 5 | 2.20 | 10.50 | 21.00 | 7.30 | 6.00 | 2.00 | 48.00/(103)[2] | 1.00 | 2.00 |

[1] E-SPHERES SL-180
[2] E-SPHERES SL-150

TABLE II

Light, Extruded Compositions
Ingredient/% wt/wt

| Comp. | Bensulfuron-methyl | Cafenstrole | Dymron | Sodium Bentonite | NEWKALGEN WG-1 | CELLOGEN WS-C | E-SPHERES SL-180/ (Avg. particle size μm) | NEWKALGEN TG-285 | NEWKALGEN EP-70G |
|---|---|---|---|---|---|---|---|---|---|
| 6 | 3.57 | 14.70 | 31.50 | 4.73 | 6.00 | 1.50 | 35.00/(115) | 1.00 | 2.00 |
| 7 | 2.68 | 11.03 | 23.63 | 5.66 | 6.00 | 2.00 | 46.00/(115) | 1.00 | 2.00 |
| 8 | 2.15 | 8.82 | 18.90 | 6.63 | 6.00 | 2.50 | 52.00/(115) | 1.00 | 2.00 |
| 9 | 1.79 | 7.35 | 16.75 | 8.11 | 6.00 | 3.00 | 54.00/(115) | 1.00 | 2.00 |

TABLE III

Light, Extruded Compositions
Ingredient/%wt/wt

| Comp. | Pyrazosul-furon-ethyl | Cafen-strole | Sodium Bentonite | NEWKALGEN WG-1 | CELLOGEN WS-C | E-SPHERES SL-180/ (Avg. particle size μm) | NEWKALGEN TG-285 | NEWKALGEN EP-70G |
|---|---|---|---|---|---|---|---|---|
| 10 | 2.21 | 22.10 | 8.69 | 8.00 | 9.00 | 53.00/(115) | 1.00 | 2.00 |
| 11 | 1.47 | 14.70 | 13.83 | 8.00 | 3.00 | 56.00/(115) | 1.00 | 2.00 |
| 12 | 1.10 | 11.00 | 13.90 | 8.00 | 3.00 | 60.00/(115) | 1.00 | 2.00 |

TABLE IV

Light, Extruded Compositions
Ingredient/%wt/Wt

| Comp. | Fenoxanil | Pyro-quilon | Methomin-ostrobin | Sodium Bentonite | NEWKALGEN WG-1 | CELLOGEN WS-C | E-SPHERES SL-180/ (Avg. particle size μm) | NEWKALGEN TG-285 | NEWKALGEN EP-70G |
|---|---|---|---|---|---|---|---|---|---|
| 13 | 50.00 | — | — | 2.00 | 6.00 | 1.00 | 38.00/(115) | 1.00 | 2.00 |
| 14 | — | 50.00 | — | 2.00 | 6.00 | 1.00 | 38.00/(115) | 1.00 | 2.00 |
| 15 | — | — | 50.00 | 2.00 | 6.00 | 1.00 | 38.00/(115) | 1.00 | 2.00 |

TABLE V

Light, Extruded Compositions
Composition Number 16

| Ingredient | % wt/wt |
|---|---|
| 1-[1-(p-Chlorophenyl)-2-fluoro-4-(4-fluoro-3-phenoxyphenyl)-2-butenyl]cyclopropane (R,S)-(Z) | 5.00 |
| Carplex #80[1] | 12.00 |
| Sodium Bentonite | 10.00 |
| NEWKALGEN WG-1 | 8.00 |
| CELLOGEN WS-C | 2.00 |
| E-SPHERES SL-180 | 60.00 |

TABLE V-continued

Light, Extruded Compositions
Composition Number 16

| Ingredient | % wt/wt |
|---|---|
| (average particle size 115 μm) | |
| NEWKALGEN TG-285 | 1.00 |
| NEWKALGEN EP-70G | 2.00 |

[1]A precipitated silica

EXAMPLE 2

Herbicidal Evaluations of Light, Extruded Compositions

A field is cultivated, muddled, sown with weed seeds (identified below), and fertilized. Five to six days later, rice seedlings (variety Chiyonishiki) at the 2.5 leaf stage are transplanted into the prepared field. The field is then divided into 100 m² (10 m×10 m) test plots using plastic plates and each plot is flooded with water to a depth of 5 cm. The flood levels are maintained at 5 cm throughout the evaluations. 20 g of composition number 1 from Example 1 and 20 g of composition number 1 from Example 1 packaged in water-soluble poly(vinyl alcohol) bags 20 g/bag are applied to the center of separate test plots to provide a rate equivalent to 60 g cyclosulfamuron, 300 g cafenstrole and 600 g dymron per hectare. After 42 days, the test plots are divided into quarters for herbicidal evaluations. These divisions are labeled as follows: point A—southwest quarter, point B—northwest quarter, point C—northeast quarter and point D — southeast quarter. Each quarter is evaluated for percent weed control compared to a check. The results are summarized in Table VI below. As can be seen from the data in Table VI, the light, extruded composition of the present invention provides control of all weed species throughout the test plots from a single application of the invention composition in the middle of each plot.

WEED SPECIES

| Code Name | Common Name | Scientific Name |
|---|---|---|
| ECHCR | Barnyardgrass | *Echinochloa crus-galli* |
| SCPJU | Bulrush, Japanese | *Scirpus juncoides* |
| MOOVA | Monochoria | *Monochoria vaginallis* |
| LIDPY | Falsepimpernel, common | *Lindernia pyxidaria* |
| SAGPY | Arrowhead | *Sagittaria pygmaea* |
| CYPSE | Flatsedge | *Cyperus serotinus* |

TABLE VI

Herbicidal Evaluations of Light, Extruded Compositions

| | | % Weed Control | | | |
|---|---|---|---|---|---|
| Treatment[1] | Weed Species | Point-A | Point-B | Point-C | Point-D |
| Composition 1 | ECHCR | 100 | 100 | 99 | 100 |
| | SCPJU | 100 | 100 | 98 | 100 |
| | MOOVA | 100 | 100 | 100 | 100 |
| | LIDPY | 99 | 100 | 97 | 97 |
| | SAGPY | 100 | 100 | 100 | 100 |
| | CYPSE | 100 | 100 | 100 | 100 |
| Composition 1 packaged in PVA bag | ECHCR | 100 | 100 | 100 | 100 |
| | SCPJU | 100 | 100 | 100 | 100 |
| | MOOVA | 100 | 100 | 100 | 100 |
| | LIDPY | 100 | 95 | 100 | 100 |
| | SAGPY | 100 | 100 | 100 | 100 |
| | CYPSE | 100 | 100 | 100 | 100 |

[1]All treatments are applied at a rate to provide the equivalent of 60 g cyclosulfamuron, 300 cafenstrole and 600 g dymron per hectare.

What is claimed is:

1. A light, extruded composition which comprises at least one agricultural compound; a light, extrudable, ceramic carrier; and at least one surface active agent.

2. The composition according to claim 1 which further comprises a mineral carrier and a binder.

3. The composition according to claim 2 which comprises on a weight basis about 0.5% to 75% of one or more agricultural compound(s); about 15% to 90% of the light, extrudable, ceramic carrier; about 2% to 20% of one or more surface active agent(s); about 1% to 30% of the mineral carrier; and about 0.1% to 10% of the binder.

4. The composition according to claim 1 wherein the light, extrudable, ceramic carrier has a density of about 0.5 g/cm³ to 0.8 g/cm³.

5. The composition according to claim 1 wherein the light, extrudable, ceramic carrier is prepared from a composition which comprises on a weight basis about 50% to 60% silicon(IV) oxide, about 25% to 45% aluminum oxide, about 0.1% to 6% calcium oxide, about 0.1% to 3% iron(III) oxide and about 0.1% to 2% titanium(IV) oxide.

6. The composition according to claim 1 wherein the light, extrudable, ceramic carrier has an average particle size of about 100 μm to 250 μm.

7. The composition according to claim 1 wherein the light, extrudable, ceramic carrier has a pressure strength greater than about 150 kg/cm².

8. The composition according to claim 1 wherein the agricultural compound is selected from the group consisting of a herbicide, an insecticide, an acaricide, a nematicide, a fungicide, a molluscicide, a plant growth regulator, a safener, an algicide and a mildewicide and mixtures thereof.

9. The composition according to claim 8 wherein the herbicide is selected from the group consisting of 2,4-D, 2,4-D-2-ethylhexyl, 2,4-D-isobutyl, 2,4-D-butyl, 2,4-D-calcium, 2,4-D-dimethylammonium, 2,4-D-diolamine, 2,4-D-isooctyl, 2,4-D-isopropyl, 2,4-D-potassium, 2,4-D-sodium, 2,4-D-trolamine, azimsulfuron, bensulfuron-methyl, bentazone, benzofenap, bifenox, bromobutide, butachlor, cafenstrole, chlormethoxynil, chlornitrofen, chlorthiamid, cinmethylin, cinosulfuron, clomeprop, cyclosulfamuron, cyclosulfamuron sodium salt, cyhalofop-butyl, dimepiperate, dimethametryn, dithiopyr, dymron, esprocarb, ethoxysulfuron, etobenzanid, fentrazamid, imazosulfuron, MCPA, MCPA-butyl, MCPA-calcium, MCPA-dimethylammonium, MCPA-isooctyl, MCPA-potassium, MCPA-sodium, MCPB, MCPB-ethyl, MCPB-sodium, MCPCA, mefenacet, molinate, naproanilide, oxadiazon, oxaziclomefone, pendimethalin, pentoxazone, piperophos, pretilachlor, prometryn, propanil, pyrazolate, pyrazosulfuron-ethyl, pyrazoxyfen, pyributicarb, simetryn, swep, thenylchlor and thiobencarb and mixtures thereof; the insecticide is selected from the group consisting of acephate, alpha-cypermethrin, benfuracarb, bensultap, BPMC, buprofezin, carbaryl, carbofuran, carbosulfan, cartap, chlorfenapyr, chlorfenvinphos, chlorpyrifos-methyl, chlorpyrifos, cyanofenphos, cycloprothrin, diazinon, dimethoate, dioxabenzofos, disulfoton, EPN, ethofenprox, fenitrothion, fenthion, furathiocarb, isoprocarb, methyl isothiocyanate, isoxathion, malathion, methomyl, metolcarb, monocrotophos, nitenpyram, phenthoate, pirimiphos-ethyl, pirimiphos-methyl, propaphos, propoxur, pyraclofos, pyridaphenthion, quinalphos, tetrachlorvinphos, thiocyclam, thiodicarb, trichlorphon, vamidothion, XMC, xylylcarb, and 1-[1-(p-chlorophenyl)-2-fluoro-4-(4-fluoro-3-phenoxyphenyl)-2-butenyl]cyclopropane (R,S)-(Z), and mixtures thereof; and the fungicide is selected from the group consisting of benomyl, captan, diclomezine, edifenphos, fenoxanil, ferimzone, flutolanil, thalide, iprobenfos, iprodione, isoprothiolane, kasugamycin, kasugamycin hydrochloride hydrate, mepronil, metalaxyl, methominostrobin, oxolinic acid, pencycuron, probenazole, pyroquilon, tecloftalam, thiophanate-methyl, TPN, tricyclazole, triflumizole and validamycin and mixtures thereof.

10. The composition according to claim 1 wherein the agricultural compound is selected from the group consisting of cyclosulfamuron, cafenstrole and dymron and mixtures thereof.

11. The composition according to claim 1 wherein the surface active agent is selected from the group consisting of an alkyl benzene sulfonate, an alkyl naphthalene sulfonate, a lignosulfonate, a naphthalene sulfonate-formaldehyde condensate, an alkyl naphthalene sulfonate-formaldehyde condensate, a polyoxyethylene alkyl ether, a polyoxyethylene alkyl ether sulfate, a polyoxyethylene alkyl ether phosphate, a polyoxyethylene alkyl aryl ether, a polyoxyethylene alkyl aryl ether sulfate, a polyoxyethylene alkyl aryl ether phosphate, a polycarboxylate, a sodium tripolyphosphate, a hexameta phosphate, a phenol sulfonate, an alkyl sulfate, a dialkyl sulfosuccinate, an alkyl ether sulfate and an acetylene glycol and mixtures thereof.

12. The composition according to claim 11 wherein the surface active agent is selected from the group consisting of an alkyl naphthalene sulfonate, a polycarboxylate, a naphthalene sulfonate-formaldehyde condensate and a dialkyl sulfosuccinate and mixtures thereof.

13. The composition according to claim 12 wherein the surface active agent comprises a mixture of a sodium alkyl naphthalene sulfonate, a polycarboxylate, a sodium naphthalene sulfonate-formaldehyde condensate and a sodium alkyl sulfonated alkylate.

14. The composition according to claim 2 wherein the mineral carrier is selected from the group consisting of calcium bentonite, sodium bentonite, montmorillonite, kaolin clay, pyrophyllite clay, sericite clay, diatomaceous earth and talc and mixtures thereof.

15. The composition according to claim 14 wherein the mineral carrier is sodium bentonite.

16. The composition according to claim 2 wherein the binder is selected from the group consisting of sodium carboxymethyl cellulose, hydroxy methyl cellulose, methyl cellulose, ethyl cellulose, dextrin, starch, poly(vinyl alcohol), sodium alginate, sodium polyacrylate, xanthan gum, welan gum and gum arabic and mixtures thereof.

17. The composition according to claim 16 wherein the binder is sodium carboxymethyl cellulose.

18. The composition according to claim 2 which comprises on a weight basis about 0.2% to 7% cyclosulfamuron; about 10% to 20% cafenstrole; about 25% to 35% dymron; about 25% to 45% of a light, extrudable, ceramic carrier which: (1) is prepared from a composition which comprises on a weight basis about 50% to 60% silicon(IV) oxide, about 25% to 45% aluminum oxide, about 0.1% to 6% calcium oxide, about 0.1% to 3% iron(III) oxide and about 0.1% to 2% titanium(IV) oxide, (2) has an average particle size of about 100 μm to 250 μm, and (3) has a pressure strength greater than about 150 kg/cm$^2$; about 4% to 8% of a sodium alkyl naphthalene sulfonate; about 0.5% to 2% of a mixture of a polycarboxylate and a sodium naphthalene sulfonate-formaldehyde condensate; about 1% to 3% of a sodium alkyl sulfonated alkylate; about 3% to 8% sodium bentonite; and about 1% to 3% sodium carboxymethyl cellulose.

19. A method for applying at least one agricultural compound to the water of paddy fields which comprises applying to the water surface of the paddy fields a light, extruded composition comprising at least one agricultural compound; a light, extrudable, ceramic carrier; and at least one surface active agent.

20. The method according to claim 19 wherein the light, extruded composition further comprises a mineral carrier and a binder.

21. The composition according to claim 19 wherein the light, extrudable, ceramic carrier has a density of about 0.5 g/cm$^3$ to 0.8 g/cm$^3$.

22. The method according to claim 19 wherein the light, extrudable, ceramic carrier is prepared from a composition which comprises on a weight basis about 50% to 60% silicon(IV) oxide, about 25% to 45% aluminum oxide, about 0.1% to 6% calcium oxide, about 0.1% to 3% iron(III) oxide and about: 0.1% to 2% titanium(IV) oxide.

23. The method according to claim 19 wherein the light, extrudable, ceramic carrier has an average particle size of about 100 μm to 250 μm.

24. The method according to claim 19 wherein the light, extrudable, ceramic carrier has a pressure strength greater than about 150 kg/cm$^2$.

25. The method according to claim 19 wherein the agricultural compound is selected from the group consisting of a herbicide, an insecticide, an acaricide, a nematicide, a fungicide, a molluscicide, a plant growth regulator, a safener, an algicide and a mildewicide and mixtures thereof.

26. The method according to claim 19 wherein the agricultural compound is selected from the group consisting of cyclosulfamuron, cafenstrole and dymron and mixtures thereof.

27. The method according to claim 20 wherein the surface active agent comprises a mixture of a sodium alkyl naphthalene sulfonate, a polycarboxylate, a sodium naphthalene sulfonate-formaldehyde condensate and a sodium alkyl sulfonated alkylate; the mineral carrier is sodium bentonite; and the binder is sodium carboxymethyl cellulose.

28. The method according to claim 19 wherein the light, extruded composition is packaged in a contained, water-soluble delivery system and the packaged, light, extruded composition is applied to the water surface.

29. The method according to claim 28 wherein the contained, water-soluble delivery system is selected from the group consisting of a water-soluble poly(vinyl alcohol) bag, a water-soluble paper bag and a water-soluble bottle.

30. The method according to claim 19 wherein the light, extruded composition is packaged in an uncontained system and the uncontained, light, extruded composition is applied to the water surface by hand, spoon, aerial or mechanical application.

31. The method according to claim 30 wherein the uncontained system is selected from the group consisting of a bag, a tube and a hopper.

32. A process for the preparation of a light, extruded composition comprising at least one agricultural compound; a light, extrudable, ceramic carrier; and at least one surface active agent, which process comprises the steps of:
  (a) mixing the agricultural compound; the light, extrudable, ceramic carrier; and the surface active agent with water to obtain an extrudable mixture;
  (b) extruding the extrudable mixture from step (a) to obtain an extrudate; and
  (c) drying the extrudate to obtain the light, extruded composition.

33. The process according to claim 32 wherein step (a) further comprises a mineral carrier and a binder.

* * * * *